United States Patent [19]
Nishtala

[11] Patent Number: 6,165,136
[45] Date of Patent: Dec. 26, 2000

[54] SEMI-AUTOMATIC BIOPSY DEVICE AND RELATED METHOD OF USE

[75] Inventor: Srinivas Nishtala, Bloomington, Ind.

[73] Assignee: SCIMED Life Systems, Inc., Maple Grove, Minn.

[21] Appl. No.: 09/219,344

[22] Filed: Dec. 23, 1998

[51] Int. Cl.[7] .................................................. A61B 10/00
[52] U.S. Cl. ........................................... 600/564; 604/185
[58] Field of Search ..................................... 600/564, 565, 600/567; 604/158, 164, 166; 606/174

[56] References Cited

U.S. PATENT DOCUMENTS

| Re. 34,056 | 9/1992 | Lindgren et al. . |
| 4,699,154 | 10/1987 | Lindgren . |
| 4,702,260 | 10/1987 | Wang . |
| 4,838,280 | 6/1989 | Haaga . |
| 4,907,598 | 3/1990 | Bauer . |
| 4,917,100 | 4/1990 | Nottke . |
| 4,924,878 | 5/1990 | Nottke . |
| 4,940,468 | 7/1990 | Petillo . |
| 4,953,558 | 9/1990 | Akerfeldt . |
| 4,958,625 | 9/1990 | Bates et al. . |
| 4,976,269 | 12/1990 | Mehl . |
| 5,014,717 | 5/1991 | Lohrmann . |
| 5,127,419 | 7/1992 | Kaldany . |
| 5,161,542 | 11/1992 | Palestrant ................................. 600/567 |
| 5,172,702 | 12/1992 | Leign et al. ............................. 600/567 |
| 5,188,118 | 2/1993 | Terwilliger . |
| 5,195,533 | 3/1993 | Chin et al. . |
| 5,249,582 | 10/1993 | Taylor . |
| 5,282,476 | 2/1994 | Terwilliger . |
| 5,313,958 | 5/1994 | Bauer ...................................... 128/754 |
| 5,355,871 | 10/1994 | Hurley et al. . |
| 5,368,045 | 11/1994 | Clement et al. . |
| 5,388,589 | 2/1995 | Davis . |
| 5,394,887 | 3/1995 | Haaga . |
| 5,415,182 | 5/1995 | Chin et al. . |
| 5,425,376 | 6/1995 | Banys et al. . |
| 5,462,062 | 10/1995 | Rubinstein et al. . |
| 5,480,388 | 1/1996 | Zadini et al. . |
| 5,487,392 | 1/1996 | Haaga . |
| 5,505,210 | 4/1996 | Clement . |
| 5,505,211 | 4/1996 | Ohto et al. . |
| 5,507,298 | 4/1996 | Schramm et al. . |
| 5,511,556 | 4/1996 | DeSantis . |
| 5,538,010 | 7/1996 | Darr et al. . |
| 5,546,957 | 8/1996 | Heske . |
| 5,551,442 | 9/1996 | Kanner et al. . |
| 5,578,053 | 11/1996 | Yoon . |
| 5,669,923 | 9/1997 | Gordon . |
| 5,674,232 | 10/1997 | Halliburton . |
| 5,842,999 | 12/1998 | Pruitt et al. ............................. 600/562 |
| 6,083,176 | 7/2000 | Terwilliger ............................. 600/562 |

FOREIGN PATENT DOCUMENTS

| 92/00040 | 1/1992 | WIPO . |

*Primary Examiner*—Cary O'Connor
*Assistant Examiner*—Pamela L. Wingood
*Attorney, Agent, or Firm*—Finnegan, Henderson, Garrette, Farabow, & Dunner, L.L.P.

[57] ABSTRACT

A tissue sampling device, comprising a stylet having a notch therein and a cannula at least partially surrounding the stylet. The notch has an exposed portion for receiving tissue to be sampled, and the cannula is adjustable relative to the stylet to vary the size of the exposed portion and therefore the amount of tissue to be sampled. The device also comprises a trigger mechanism operatively connected to at least one of the cannula and the stylet. Actuation of the trigger mechanism causes relative movement of the stylet with respect to the cannula for collection of a tissue sample.

18 Claims, 8 Drawing Sheets

SEMI-AUTOMATIC BIOPSY DEVICE AND RELATED METHOD OF USE

BACKGROUND OF THE INVENTION

1. Field of the Invention

The present invention relates to a biopsy device, and more specifically to a semi-automatic biopsy device in which the user may confirm the position of the stylet tip near the target tissue area and existence of target tissue in the stylet notch before the user fires the cannula to resect the target tissue. The present invention also relates to a biopsy device which can be adjusted to take tissue samples of varying sizes, and which has a locking mechanism to avoid inadvertent resection of tissue.

2. Discussion of the Related Art

A biopsy device is a surgical instrument which allows a medical doctor to obtain a tissue sample from a patient for diagnostic purposes, and which has particular application to removing internal tissue samples from the patient's body.

Biopsy devices typically fall into three categories: manual; automatic; and semi-automatic. Automatic biopsy devices typically include a hollow cannula through which a stylet extends. The stylet includes a tip at its distal end for insertion into a patient and a notch, adjacent the tip, in which tissue prolapses. The stylet and cannula are attached to hubs which interface with compression springs. In operation, the user first "cocks" the device external to the patient to compress the springs and prepares the biopsy device for firing. "Firing" the biopsy device refers to rapid movement of the stylet or the cannula at speeds designed to minimize patient tissue trauma. Once the user cocks the device, the user inserts the device into the patient to place the stylet tip near the target tissue area. The user fires the stylet to penetrate the target tissue area and collect tissue in the notch. Upon completion of the stylet's firing, the device automatically fires the cannula, thereby closing the notch to resect the prolapsed tissue.

A disadvantage of such prior art automatic biopsy devices is that when the user positions the stylet tip near the target tissue area, the user cannot confirm collection of target tissue into the stylet notch prior to automatic firing of the cannula. A semi-automatic biopsy device allows a user to confirm prolapse of target tissue in the stylet notch. With a semi-automatic device, the user manually advances the stylet into the target tissue area. The user then may confirm correct positioning and prolapse of tissue in the notch by appropriate imaging methods before resection of the target tissue by firing the cannula.

Stylets of conventional semi-automatic devices typically resect a fixed, invariable tissue sample size. Due to the varied applications for biopsy devices in different parts of the anatomy (e.g., liver, lungs, throat, breast, etc.), the user often must take tissue biopsies of varied size. Therefore, a conventional biopsy device may not be suitable for all diagnostic applications.

In addition, conventional semi-automatic devices often utilize the same trigger mechanism to fire both the stylet and the cannula. The user typically presses the trigger mechanism to fire the stylet and to fire the cannula. With such a device, the user does not have an opportunity to confirm correct positioning of the stylet.

SUMMARY OF THE INVENTION

An object of the invention, therefore, is to provide an improved biopsy device wherein the resected sample is verified prior to actuating the biopsy device. In particular, and by no means limiting, an object of the invention includes a biopsy device which allows the user to vary the amount of notch which is exposed from the cannula as needed for a particular tissue sample size and application of the device. The area of the notch exposed determines the resulting tissue sample size. A further object of the invention includes providing a locking mechanism on a semi-automatic biopsy device which prevents inadvertent firing of the cannula.

The following description sets forth additional objects and advantages of the invention, which will be obvious from the description, or may be learned by practice of the invention. The elements and combinations particularly pointed out in the appended claims realize and attain the objects and advantages of the invention.

To achieve these objects in accordance with the purpose of the invention, the invention comprises a tissue sampling device. The device comprises a stylet having a notch therein and a cannula at least partially surrounding the stylet. The notch has an exposed portion for receiving tissue to be sampled, and the cannula is adjustable relative to the stylet to vary the size of the exposed portion and therefore the amount of tissue to be sampled. The device also comprises a trigger mechanism operatively connected to at least one of the cannula and the stylet. Actuation of the trigger mechanism causes relative movement of the stylet with respect to the cannula for collection of a tissue sample.

According to another aspect, the invention comprises a tissue sampling device, comprising a stylet having a notch therein and a cannula at least partially surrounding the stylet. The notch has an exposed portion for receiving tissue to be sampled. The device also comprises a trigger mechanism operatively connected to at least one of the cannula and the stylet. Actuation of the trigger mechanism causes relative movement of the stylet with respect to the cannula for collection of a tissue sample. The trigger mechanism operatively connects to at least one of the stylet and the cannula so that relative movement of the stylet with respect to the cannula for collection of a tissue sample occurs independently of positioning of the notch at a site of tissue to be sampled.

According to a further aspect, the invention comprises a tissue sampling device, comprising a stylet having a notch, a cannula at least partially surrounding the stylet, and a trigger mechanism operatively connected to at least one of the cannula and the stylet. Actuation of the trigger mechanism causes relative movement of the stylet with respect to the cannula for collection of a tissue sample. The device also comprises a locking mechanism operatively connected to the trigger mechanism for selectively preventing relative movement between the cannula and the stylet after the stylet has been inserted into the patient and before the stylet moves with respect to the cannula for collection of a tissue sample.

According to a further aspect, the invention comprises a method of sampling tissue. The method comprises providing a tissue sampling device having a stylet with a notch therein. The stylet is at least partially surrounded by a cannula. The method also comprises moving the cannula relative to the stylet to adjust an amount of the notch which is exposed by the cannula and therefore the amount of tissue to be sampled, advancing an end of the stylet into a target tissue area so that target tissue prolapses into the exposed amount of the notch, and effecting relative movement of the cannula and the stylet such that the cannula resects and collects the target tissue in the notch.

According to a further aspect, the invention comprises a method of sampling tissue. The method comprises providing a tissue sampling device having a stylet with a notch therein. The stylet is at least partially surrounded by a cannula. The method also comprises advancing an end of the stylet into a target tissue area so that target tissue prolapses into the notch, releasing a locking mechanism to allow relative movement of the cannula and the stylet for collecting target tissue in the notch, and effecting relative movement of the cannula and the stylet such that the cannula resects and collects the target tissue in the notch.

The foregoing general description and the following detailed description are exemplary and explanatory only and are not restrictive of the invention as claimed.

BRIEF DESCRIPTION OF THE DRAWINGS

The accompanying drawings are included to provide a further understanding of the invention and are incorporated in and constitute part of the specification, illustrate preferred embodiments of the invention, and, together with a description, serve to explain the principles of the invention.

DETAILED DESCRIPTION OF THE PREFERRED EMBODIMENTS

Reference will be made in detail to the present preferred embodiments of the invention. The accompanying drawings illustrate examples of a preferred embodiment of the invention. Like reference numerals refer to like parts in the various figures of the drawings.

The present invention is directed to a biopsy device having a stylet which interacts with a cannula to collect a tissue sample. The biopsy device of the present invention includes a number of features to aid in collection of target tissue. For example, a user may move the stylet and cannula relative to each other to adjust the amount of notch exposed by the cannula. This allows the user to adjust the size of tissue sample taken each time he uses the biopsy device. The user can select an infinite number of tissue sample sizes based upon the application of this device to different parts of the patient's anatomy. In addition, the biopsy device of the present invention is semi-automatic and therefore allows the user to confirm the prolapse of target tissue into the stylet notch before firing the cannula to resect the tissue. The biopsy device of the present invention also prevents inadvertent firing of the cannula. For example, a biopsy device of the present invention employs a locking mechanism to prevent inadvertent cannula firing before the user confirms the presence of target tissue in the stylet notch. Certain embodiments of the device according to the invention collect more than one tissue sample without removing the stylet from the patient. This is accomplished, for example, by having a notch which extends throughout the stylet to evacuate the sample, or by having a detachable cannula and stylet.

When operating a biopsy device according to the present invention, the user manually advances the stylet of the biopsy device in the fired/free state into the tissue area of interest and then manually cocks the biopsy device and fires the cannula independent of completion of the stylet stroke. One benefit of this manual actuation feature is that the user can confirm the correct location of the stylet prior to cocking the biopsy device, and the prolapse of target tissue into the stylet notch prior to firing the cannula.

Figure 1:
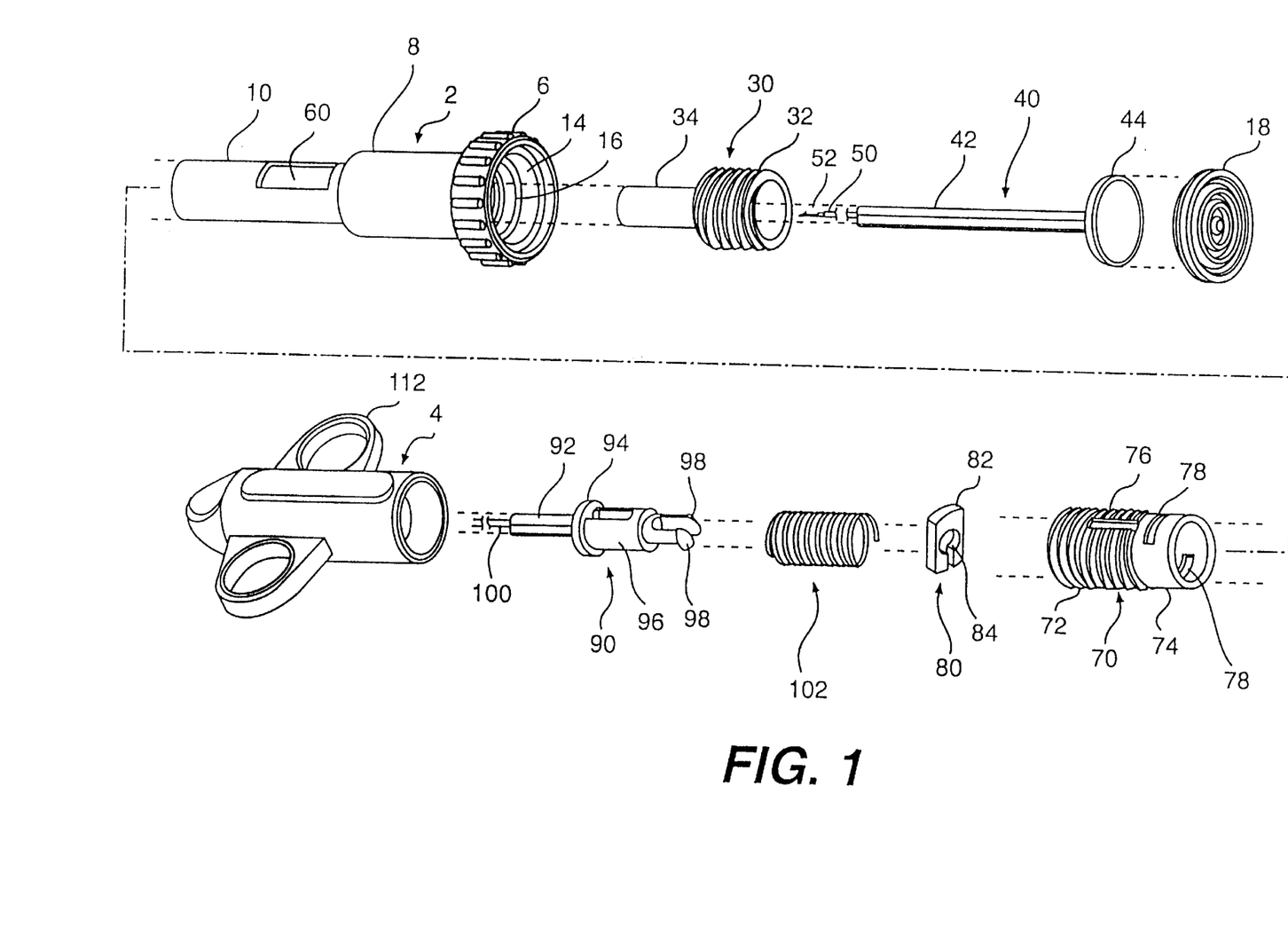
FIG. 1 is an exploded perspective view of a biopsy device according to an embodiment of the present invention.

FIG. 1 presents an exploded view of a biopsy device of the present invention. Reference numeral 1 designates the biopsy device which includes, in a preferred embodiment, the following interrelated parts: a housing (4); a dial (2); dial cap (18); a snap-adjust (30); a stylet hub (40); a stylet (50); a float (70); a back stop (80); a coil spring (102); a cannula hub (90); and a cannula (100). These parts are hereinafter described. Devices according to the present invention may be made in more or less parts and still be within the scope of the invention.

When the biopsy device of the present invention is assembled, a dial 2 is partially inserted into a housing 4. Dial 2 and housing 4 are preferably substantially cylindrical. The user manipulates dial 2 to adjust the cannula relative to the stylet, and to fire the stylet and the cannula. Dial 2 includes a gripping portion 6, a central portion 8, and a narrow portion 10.

Also when the biopsy device is fully assembled, narrow portion 10 of dial 2 is at least partially inserted into housing 4. Dial 2 has a bore of varying diameter extending therethrough. Gripping portion 6 of dial 2 has a stepped bore which includes a first dial shoulder 14 and a second dial shoulder 16. A dial cap 18 closes gripping portion 6 of dial 2 and rests against first dial shoulder 14. Central portion 8 of dial 2 has a left-handed inner threaded bore with a substantially constant diameter. Narrow portion 10 of dial 2 has a substantially constant diameter, as shown in FIGS. 2 through 7, and a front wall 20 which extends axially inwardly to form a narrow aperture 22. Housing 4 has an inner threaded bore 24 and a housing shoulder 26 which transitions inner threaded bore 24 into a narrow aperture 28. Inner threaded bore 24 has a right-handed thread.

A snap-adjust 30 extends within dial 2, and has an externally threaded portion 32 and a narrow unthreaded portion 34. Snap adjust 30 interacts with the cannula hub to fire the cannula, and has a bore extending therethrough and a narrow aperture 38. Snap-adjust 30 threads into dial 2 by engagement of externally threaded portion 32 of snap-adjust 30 with the inner threaded bore of dial 2 until it reaches a desired position.

Figure 8:
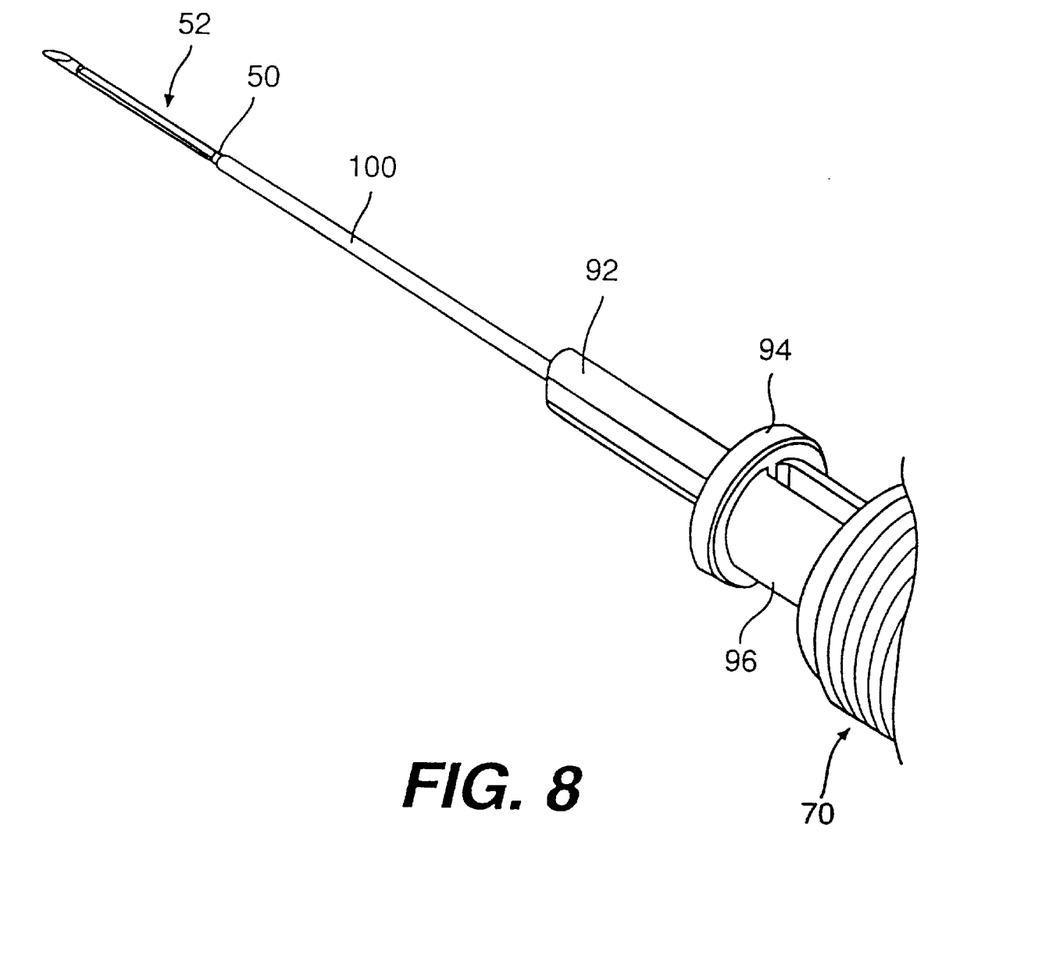
FIG. 8 is a perspective view of the stylet and cannula of the assembled biopsy device of FIG. 1.

A stylet hub 40 extends through snap-adjust 30, such that a stem 42 of stylet hub 40 extends through narrow aperture 38 of snap-adjust 30, preferably until a base 44 of stylet hub 40 abuts second dial shoulder 16. Stylet hub 40 holds a stylet 50, for example by insert molding stylet 50 into stem 42. Stylet 50 has a notch 52 at a distal end thereof (see FIG. 8). In a preferred embodiment, notch 52 has a length of about 1 inch, but the amount of notch 52 which is exposed by cannula 100 may vary as desired by the user.

Snap-adjust 30 has, at an end 56 thereof, walls 58 which slope radially outward from aperture 38. Walls 58 are sloped to release (cam) locking arms 98 of cannula hub 90 as described below. In addition, dial 2 has two cut-outs 60 on opposing sides of its narrow portion 40 which are sized to accept a back stop 80 described below. A float 70 extends around narrow portion 10 of dial 2, and is positioned between narrow portion 10 of the dial 2 and inner threaded bore 24 of housing 4. Float 70 has an externally threaded portion 72 which engages inner threaded bore 24 of housing 4. Float 70 also has an unthreaded portion 74. A longitudinally elongate cut-out 76 (see FIGS. 1 and 5) extends through externally threaded portion 72 of float 70. Two circumferentially elongate cut-outs 78 are provided on opposing sides of unthreaded portion 74 of float 70. When the biopsy device is fully assembled, cut-outs 60 of dial 2 align with circumferentially elongate cut-outs 78 of float 70.

A back stop 80 engages dial 2 and float 70 to ensure that as dial 2 rotates, so does float 70. To do so, back stop 80 has opposing edges 82 which extend through and engage cut-outs 60 of dial 2 and circumferentially elongate cut-outs 78 of float 70. There need not be two dial cut-outs 60 and two circumferentially elongate cut-outs 78 with back stop 80 extending therethrough. The present invention contemplates any suitable method for engaging back stop 80, dial 2 and float 70. Back stop 80 further includes an aperture 84 which receives locking arms 98 of cannula hub 90 when the biopsy device is cocked.

A cannula hub 90 extends within narrow portion 10 of dial 2 and releasibly engages back stop 80. Cannula hub 90 includes a stem 92 on one side of a flange 94, and a cylindrical body 96 on the other side of flange 94. Releasable locking arms 98 extend from cylindrical body 96 and releasibly engage back stop 80 by insertion through back stop aperture 84. Flange 94 abuts front wall 20 of dial 2. A cannula 100 is affixed to stem 92 of cannula hub 90, for example by insert molding cannula 100 into stem 92. Cannula 100 is preferably hollow and at least partially surrounds stylet 50.

A resilient member 102 biases cannula hub 90 away from back stop 80, and is compressed when the biopsy device is cocked. Resilient member 102 is preferably a coil spring surrounding cylindrical body 96 of cannula hub 90, but may also include a leaf spring or other suitable resilient member. Resilient member 102 extends between flange 94 of cannula hub 90 and back stop 80.

Figure 2:
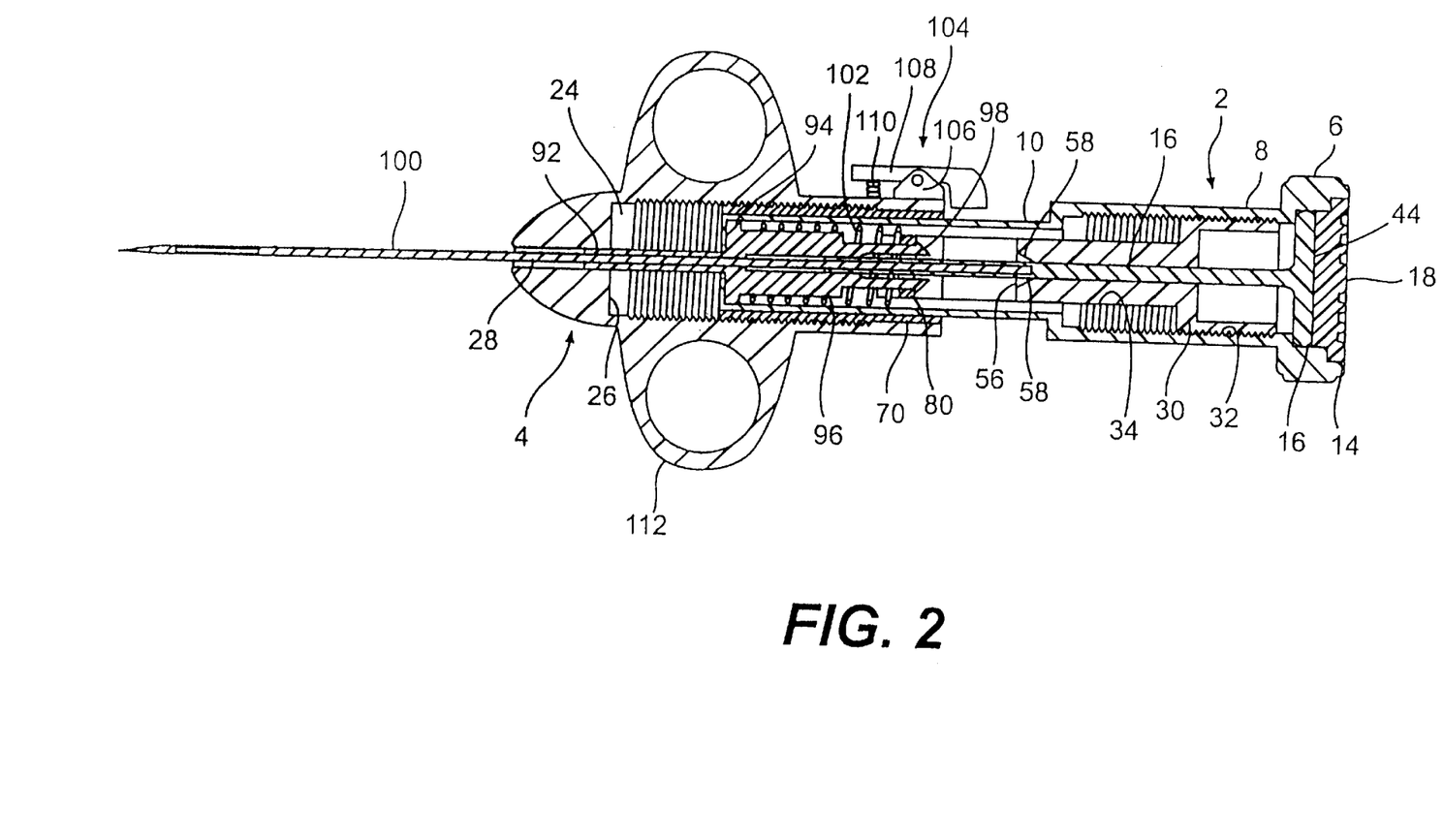
FIG. 2 is a cross-sectional top view of the assembled biopsy device of FIG. 1 in a cocked state, including an optional locking mechanism.
Figure 3:
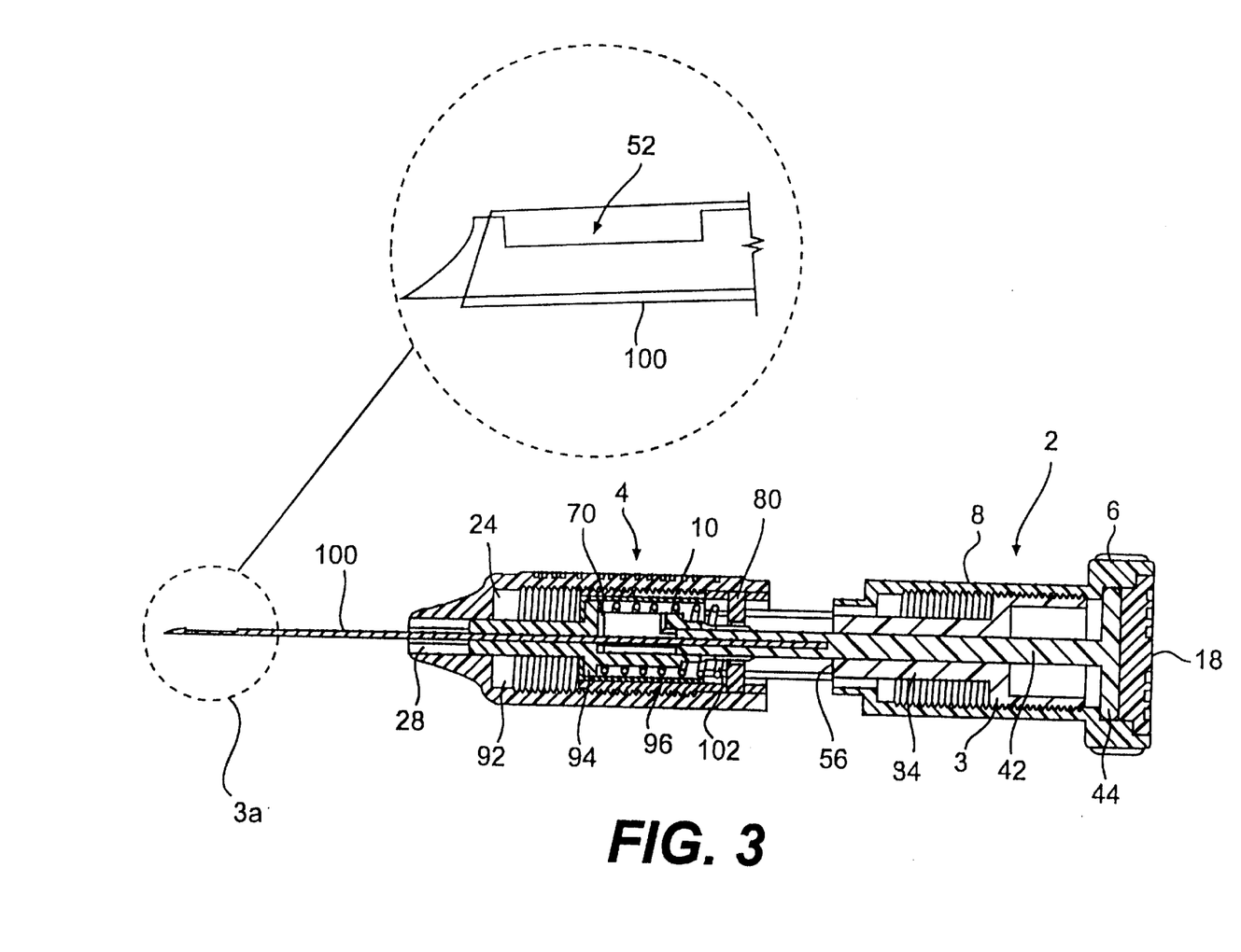
FIG. 3 is a cross-sectional side view of the assembled biopsy device of FIG. 1 in a cocked state.
Figure 4:
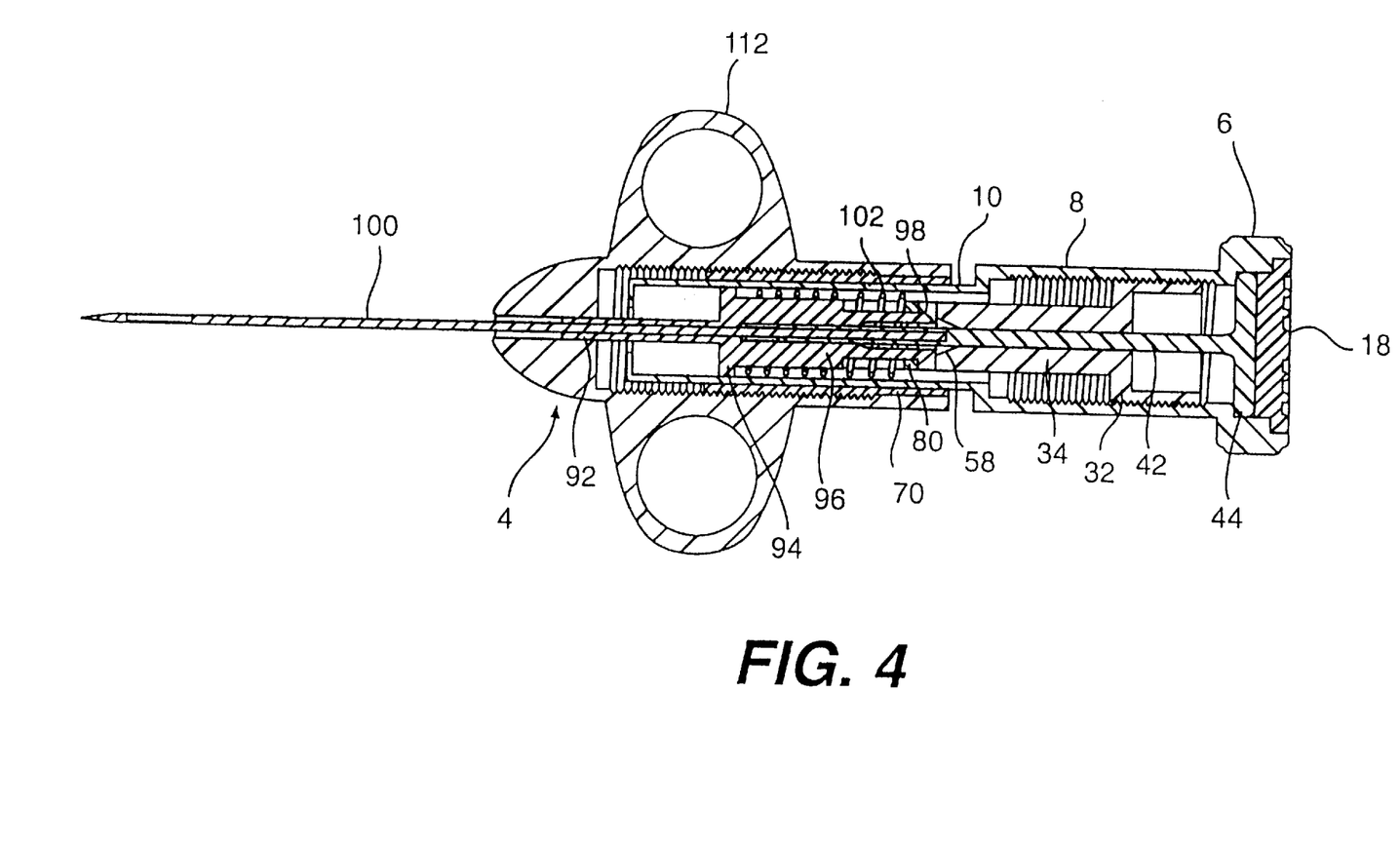
FIG. 4 is a cross-sectional top view of the assembled biopsy device of FIG. 1 in a trip state.
Figure 5:
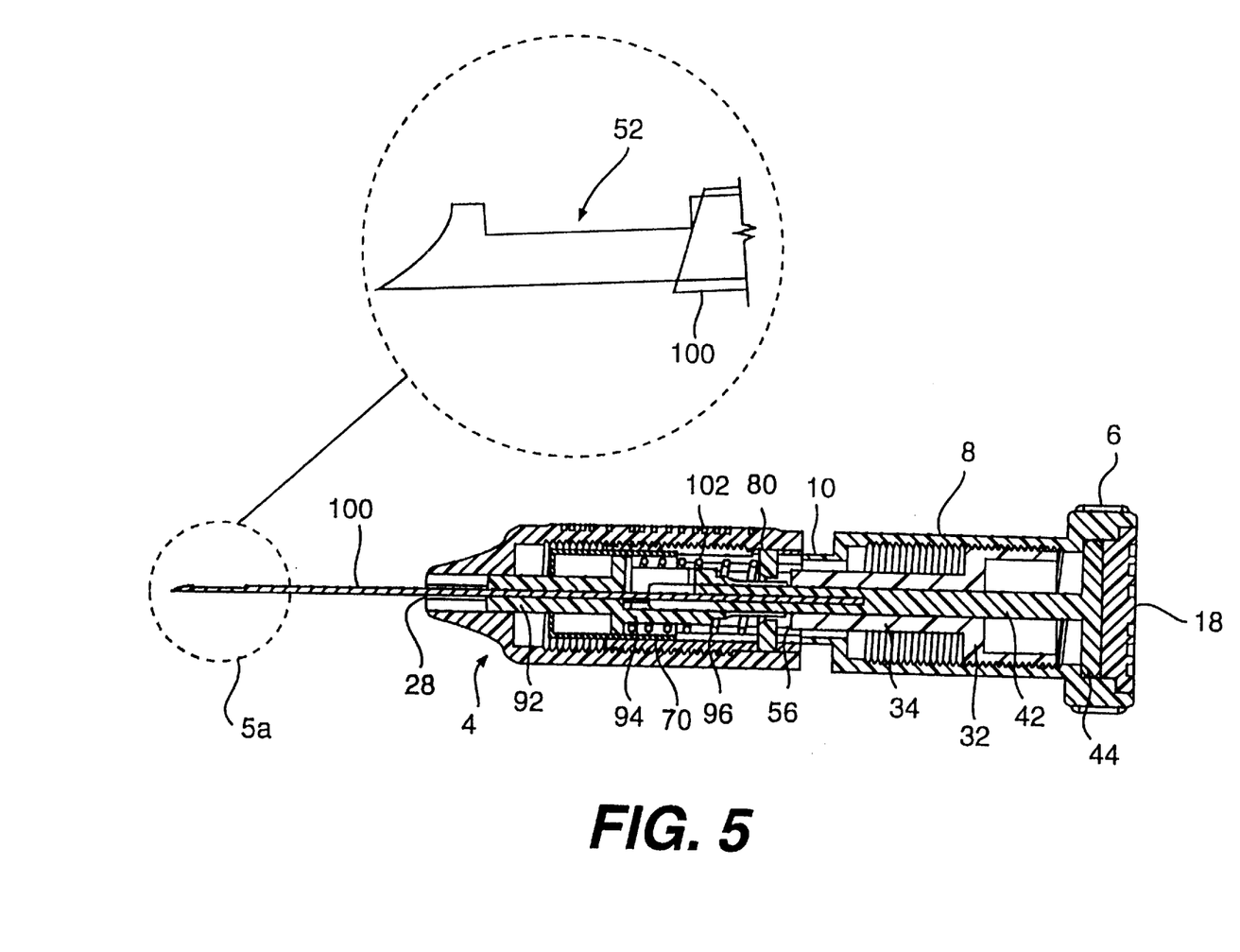
FIG. 5 is a cross-sectional side view of the assembled biopsy device of FIG. 1 in a trip state.
Figure 6:
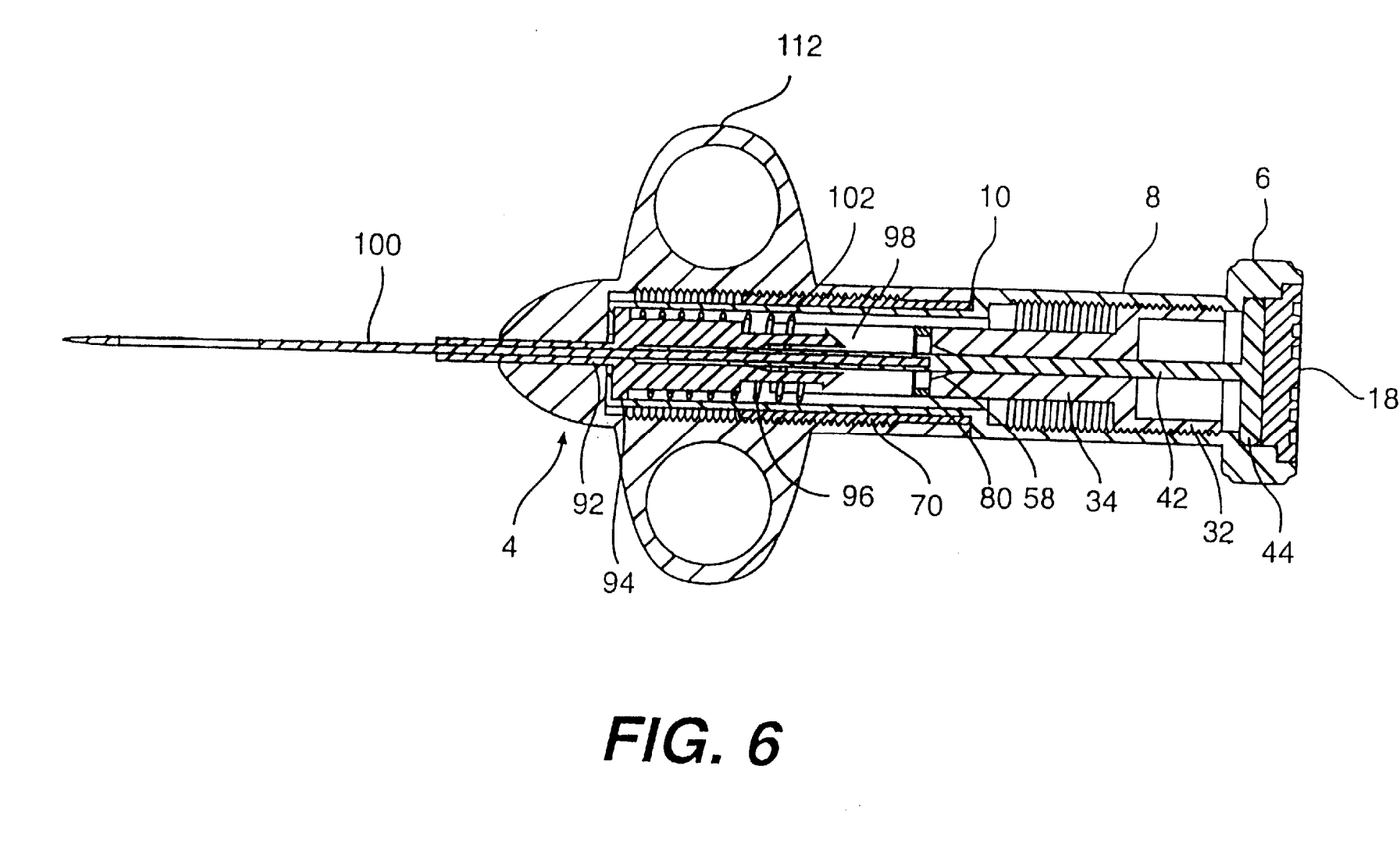
FIG. 6 is a cross-sectional top view of the assembled biopsy device of FIG. 1 in a fired/free state.
Figure 7:
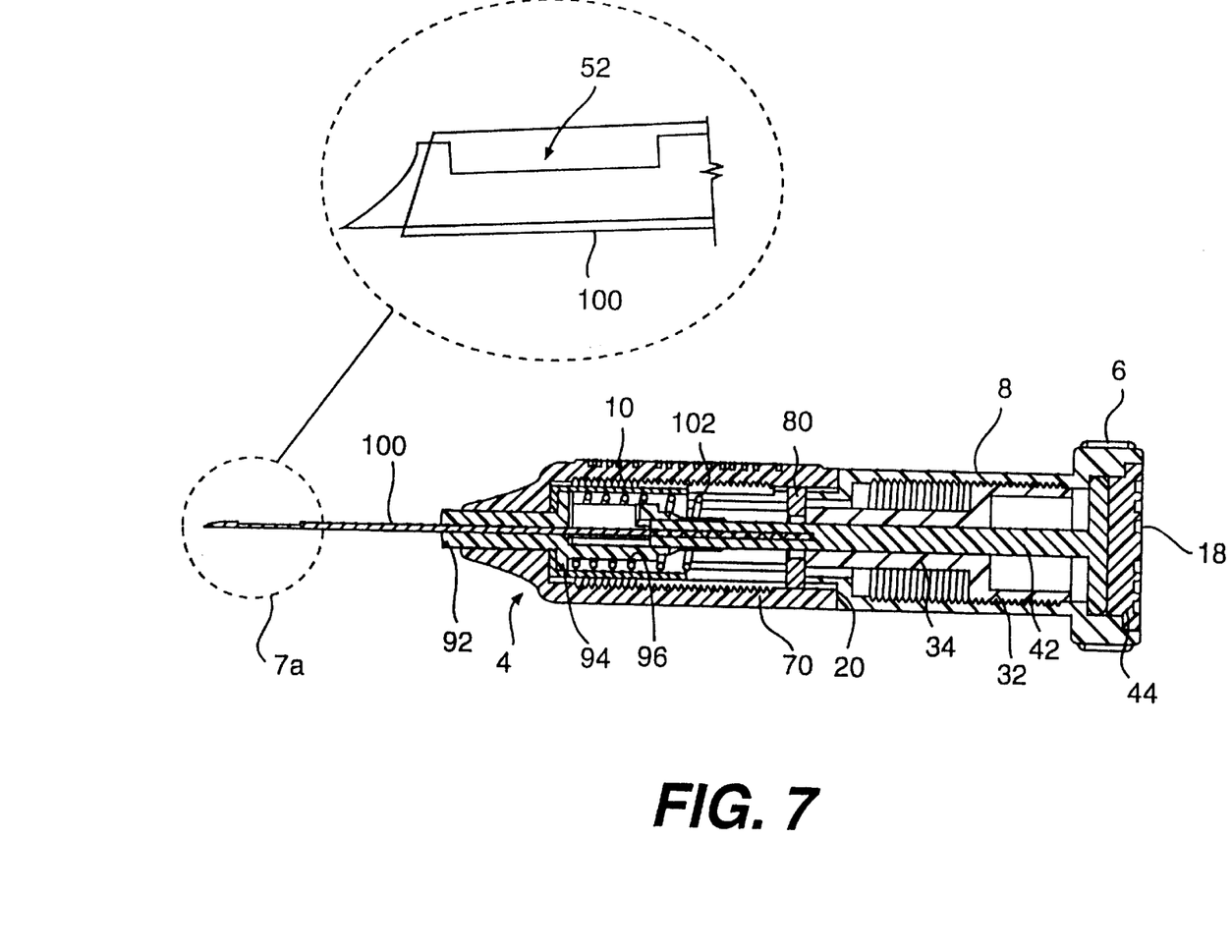
FIG. 7 is a cross-sectional side view of the assembled biopsy device of FIG. 1 in a fired/free state.

Operation of the biopsy device of the present invention will be described with specific reference to FIGS. 2 through 7. FIGS. 2 and 3 illustrate cross-sections of the biopsy device of the present invention in its cocked state. FIGS. 4 and 5 illustrate cross-sections of the biopsy device of the present invention in its trip state. FIGS. 6 and 7 illustrate cross-sectional views of the biopsy device of the present invention in its fired/free state. When the stylet of the biopsy device is inserted into the patient, the biopsy device is in a fired/free state wherein stylet notch 52 is not exposed by cannula 100. After insertion of the biopsy device, the user cocks the biopsy device. To do so, the user pulls dial 2 proximally through housing 4. As the user pulls dial 2 proximally, front wall 20 of dial 2 pulls cannula hub 90 proximally and compresses resilient member 102 until releasable locking arms 98 of cannula hub 90 snap into aperture 84 of back stop 80. In addition, cocking the biopsy device moves stylet 50 and cannula 100 proximally in the housing. Stylet notch 52 remains unexposed by cannula 100.

Once the user cocks the biopsy device, the user presses dial 2 distally into housing 4. Pressing dial 2 transitions the biopsy device from the cocked state to the trip state, moving stylet hub 40 which advances stylet notch 52 to expose notch 52 from cannula 100. Exposure of stylet notch 52 allows target tissue to prolapse into notch 52. The user then confirms prolapse of tissue into stylet notch 52 through a known imaging technique, such as, for example, x-ray, ultrasound or fluoroscopy.

Once the user has confirmed the presence of target tissue in stylet notch 52, he fires cannula 100. To fire cannula 100, the user presses dial 2 further into housing 4 until sloped walls 58 of snap-adjust 30 engage releasable locking arms 98 of cannula hub 90 and press them together to release releasable locking arms 98 from back stop aperture 84. Due to the presence of compressed resilient member 102 between back stop 80 and flange 94 of cannula hub 90, when locking arms 98 are released from back stop aperture 84, resilient member 102 expands and fires cannula 100 out of housing 4. When the user fires cannula 100, cannula 100 resects and collects the tissue in stylet notch 52. Alternatively, the biopsy device of the present invention could resect tissue by moving stylet 50 proximally while cannula 100 remains fixed.

As stated above, biopsy devices have applications in different parts of the anatomy (e.g., liver, lungs, throat, breast, etc.). The size of a desired tissue sample often differs depending upon the application, making it desirable for the user to adjust the amount of stylet notch 52 exposed by the cannula as needed for a particular application. The present invention allows for variation of the tissue sample size.

To vary the sample size, the user turns dial 2 clockwise to adjust the amount of stylet notch 52 exposed by cannula 100. The following relationships between the various interrelated parts permit cannula 100 to move relative to stylet 50.

Cannula hub 90 is rotationally fixed within housing 4 due to the rectangular cross-section of its stem 94 and close-fitting housing aperture 28. Stylet hub 40 is rotationally fixed within cannula hub 90 due to the rectangular cross-section of stylet hub stem 42 and a close-fitting cannula aperture. Snap-adjust 30 is rotationally fixed with respect to stylet hub 40 due to the rectangular cross-section of stylet hub stem 42 in its narrow aperture 38. Thus, rotation of dial 2 with respect to housing 4 does not rotate cannula hub 90, cannula 100, stylet hub 40, stylet 50 or snap-adjust 30 because they are rotationally fixed with respect to housing 4. Thus, the stylet notch 52 remains in a fixed position relative to the housing. Upon clockwise rotation of dial 2, snap-adjust 30 moves axially with respect to dial 2 due to the threaded engagement between snap-adjust 30 and dial 2. Since back stop 80 has its opposing edges 82 extending through cut-outs 78 of float 70 and cut-outs 60 of dial 2, rotation of dial 2 causes rotation of float 70. Since float 70 is in threaded engagement with housing 4, rotation of float 70 moves float 70 axially with respect to housing 4. As float 70 moves along the longitudinal axis of housing 4, float 70 pulls back stop 80 axially. Cannula hub 90 moves axially with back stop 80 when its releasable locking arms 98 are engaged therewith (i.e., when the device is cocked) to move cannula 100 relative to stylet 50. Snap-adjust 30 and float 70 move the same amount along the longitudinal axis of dial 2, so that the gap between snap-adjust 30 and float 70 remains constant.

FIG. 2 shows an embodiment of the biopsy device of the present invention which includes a locking mechanism 104 for ensuring that the cannula is not inadvertently fired. Locking mechanism 104 is an optional, but preferred, feature of the device and is not shown in all of the Figures. Locking mechanism 104 preferably has a base 106 located along the periphery of housing 4, adjacent the end of housing 4 into which dial 2 is inserted. A lock arm 108 is pivotally attached to base 106. A resilient member 110, such as a coil spring, biases lock arm 108 into a gap between dial 2 and housing 4 in the cocked state and the trip state of the biopsy device. When the biopsy device is in the trip state, the user must disengage locking mechanism 104 to fire cannula 100 by pushing on lock arm 108 at a location directly over resilient member 110. This raises lock arm 108 out of the gap between housing 4 and dial 2 so that the user can press dial 2 far enough into housing 4 to fire cannula 100.

As shown in FIGS. 1, 2, 4 and 6, housing 4 preferably includes finger grips 112 which make the biopsy device easier to grip and operate. In addition, gripping portion 6 of dial 2 preferably has an irregular outer surface to improve gripping for turning dial 2, for example to adjust amount of stylet notch 52 exposed from the cannula. The irregular outer surface of gripping portion 6 is shown to be ribbed, but may have any suitable grip-enhancing surface. All of the interrelated parts, except for resilient member 102 preferably comprise a molded plastic material. Resilient member 102 preferably comprises a metal coil spring.

It will be apparent to those skilled in the art that various modifications and variations can be made to the biopsy device of the present invention without departing from the scope or spirit of the invention. Thus, the present invention is intended to cover the modifications and variations of this invention provided they come within the scope of the appended claims and their equivalents.

What is claimed is:

1. A tissue sampling device, comprising:
   a stylet having a notch therein, the notch having an exposed portion for receiving tissue to be sampled;
   a cannula at least partially surrounding the stylet, the cannula being adjustable relative to the stylet to vary the size of the exposed portion and therefore the amount of tissue to be sampled; and
   a trigger mechanism operatively connected to at least one of the cannula and the stylet, wherein actuation of the trigger mechanism causes relative movement of the stylet with respect to the cannula for collection of a tissue sample,
   wherein the trigger mechanism is adapted to be actuated in a first way to adjust the cannula relative to the stylet to vary the size of the exposed portion of the notch prior to collection of a tissue sample, and is adapted to be actuated in a second way to cause relative movement the stylet and the cannula for collection of a tissue sample.

2. The device as claimed in claim 1, wherein the trigger mechanism operatively connects to at least one of the stylet and the cannula so that relative movement of the stylet with respect to the cannula for collection of a tissue sample occurs independently of positioning of the notch at a site of tissue to be sampled.

3. The device as claimed in claim 2, wherein the trigger mechanism includes a resilient member that releases from a compressed state when the stylet moves with respect to the cannula for collection of a tissue sample.

4. The device as claimed in claim 1, further comprising a housing surrounding at least a portion of the stylet and the cannula, and
   wherein the trigger mechanism is a dial, and the dial is actuated in the first way by rotating the dial relative to the housing, and the dial is actuated in the second way by pressing the dial into the housing.

5. The device as claimed in claim 4, wherein the stylet is fixedly connected to the housing so that rotation of the trigger mechanism does not substantially rotate the stylet.

6. The device as claimed in claim 4, further comprising a locking mechanism attached to the housing, the locking mechanism having an engaged state to prevent inadvertent movement of the stylet with respect to the cannula for collection of a tissue sample.

7. The device as claimed in claim 6, wherein the locking mechanism includes a lock arm pivotally attached to the housing, the lock arm being interposed between the housing and the dial when in a locked state.

8. A tissue sampling device, comprising:
   a stylet having a notch and a cannula at least partially surrounding the stylet and movable with respect to the stylet;
   a trigger mechanism operatively connected to at least one of the cannula and the stylet, wherein actuation of the trigger mechanism causes relative movement of the stylet with respect to the cannula for collection of a tissue sample; and
   a locking mechanism operatively connected to the trigger mechanism, wherein the locking mechanism selectively prevents relative movement between the cannula and the stylet after the stylet has been inserted into the patient and before the stylet moves with respect to the cannula for collection of a tissue sample,
   wherein the locking mechanism is adapted to bias into a locked state by a resilient member.

9. The device as claimed in claim 8, wherein the locking mechanism includes a lock arm pivotally attached to the device.

10. The device as claimed in claim 9, further comprising a housing at least partially surrounding the stylet and the cannula,
    wherein the trigger mechanism includes a dial which interacts with the housing to trigger relative movement of the stylet with respect to the cannula for collection of a tissue sample, and
    wherein the lock arm is interposed between the housing and the dial when in the locked state.

11. A method of sampling tissue, comprising:
    providing a tissue sampling device having a stylet with a notch therein, the stylet being at least partially surrounded by a cannula;
    actuating a trigger mechanism to move the cannula relative to the stylet to adjust an amount of the notch exposed by the cannula and an amount of target tissue to be sampled;
    advancing an end of the stylet into a target tissue area so that the target tissue prolapses into the exposed amount of the notch; and
    effecting relative movement of the cannula and the stylet such that the cannula resects and collects the target tissue in the notch.

12. A method of sampling tissue, comprising:
    providing a tissue sampling device having a stylet with a notch therein, the stylet being at least partially surrounded by a cannula;
    moving the cannula relative to the stylet to adjust an amount of the notch exposed by the cannula and an amount of target tissue to be sampled;
    advancing an end of the stylet into a target tissue area so that the target tissue prolapses into the exposed amount of the notch;
    effecting relative movement of the cannula and the stylet such that the cannula resects and collects the target tissue in the notch; and confirming the presence of the target tissue in the notch before effecting relative movement of the cannula and the stylet to resect and collect the target tissue in the notch.

13. The method as claimed in claim 11, wherein the presence of the target tissue in the notch is confirmed by an imaging process.

14. The method as claimed in claim 11, further comprising releasing a locking mechanism before effecting relative movement of the cannula and the stylet to resect the target tissue.

15. A method of sampling tissue, comprising:

providing a tissue sampling device having a stylet with a notch therein, the stylet being at least partially surrounded by a cannula;

moving the cannula relative to the stylet to adjust an amount of the notch exposed by the cannula and an amount of target tissue to be sampled;

advancing an end of the stylet into a target tissue area so that the target tissue prolapses into the exposed amount of the notch; and effecting relative movement of the cannula and the stylet such that the cannula resects and collects the target tissue in the notch;

wherein actuating a trigger mechanism effects movement of the cannula for collection of the target tissue in the notch, and wherein the trigger mechanism is adapted to be actuated in a first way to adjust the amount of the notch which is exposed by the cannula prior to collection of the target tissue, and is adapted to be actuated in a second way to effect relative movement of the cannula and the stylet for collection of the target tissue in the notch.

16. A method of sampling tissue, comprising:

providing a tissue sampling device having a stylet with a notch therein, the stylet being at least partially surrounded by a cannula;

advancing an end of the stylet into a target tissue area so that a target tissue prolapses into the notch;

actuating a trigger mechanism to move the cannula along the stylet to adjust an amount of the notch which is exposed by the cannula and therefore an amount of the target tissue to be sampled;

releasing a locking mechanism to allow relative movement of the cannula and the stylet for collecting the target tissue in the notch; and effecting relative movement of the cannula and the stylet such that the cannula resects and collects the target tissue in the notch.

17. The method as claimed in claim 16, further comprising confirming the presence of the target tissue in the notch before releasing a locking mechanism to allow relative movement of the cannula and the stylet for collecting the target tissue in the notch.

18. The method as claimed in claim 17, wherein the presence of the target tissue in the notch is confirmed by an imaging process.

* * * * *

UNITED STATES PATENT AND TRADEMARK OFFICE
CERTIFICATE OF CORRECTION

PATENT NO. : 6,165,136

DATED: December 26, 2000

INVENTORS: Srinivas NISHTALA

It is hereby certified that errors appear in the above-identified patent and that said Letters Patent is hereby corrected as shown below:

In claim 1, col. 7, line 45, after "movement" insert --of--.

Signed and Sealed this

Twenty-ninth Day of May, 2001

Attest:

NICHOLAS P. GODICI

*Attesting Officer*     *Acting Director of the United States Patent and Trademark Office*